(12) United States Patent
Odermatt et al.

(10) Patent No.: US 8,105,619 B2
(45) Date of Patent: Jan. 31, 2012

(54) ANTIMICROBIAL MEDICOTECHNICAL PRODUCT, PROCESS FOR ITS PRODUCTION AND USE

(75) Inventors: Erich Odermatt, Schaffhausen (CH);
Ingo Berndt, Tuttlingen (DE); Joerg Tiller, Freiburg (DE); Chau Hon Ho, Freiburg (DE)

(73) Assignee: AESCULAP AG, Tuttlingen/Donau (DE)

( * ) Notice: Subject to any disclaimer, the term of this patent is extended or adjusted under 35 U.S.C. 154(b) by 915 days.

(21) Appl. No.: 12/073,560

(22) Filed: Mar. 6, 2008

(65) Prior Publication Data
US 2008/0292675 A1 Nov. 27, 2008

(30) Foreign Application Priority Data
Mar. 9, 2007 (DE) .......................... 10 2007 012 253

(51) Int. Cl.
*A61K 47/00* (2006.01)
*A01N 25/00* (2006.01)

(52) U.S. Cl. ...................... 424/405; 514/772.1; 514/773
(58) Field of Classification Search .................. None
See application file for complete search history.

(56) References Cited

U.S. PATENT DOCUMENTS
2008/0292671 A1* 11/2008 Ho et al. .................. 424/405

FOREIGN PATENT DOCUMENTS

| DE | 199 21 894 A1 | 11/2000 |
|---|---|---|
| DE | 103 23 597 | 12/2004 |
| DE | 10 2005 044 360 | 3/2007 |
| DE | 10 2005 044 360 A1 | 3/2007 |
| DE | 10 2006 011 217 A1 | 9/2007 |
| WO | 2004/056403 | 7/2004 |
| WO | 2004/056404 | 7/2004 |
| WO | 2004056404 A2 | 7/2004 |
| WO | 2004/085998 | 10/2004 |

OTHER PUBLICATIONS

Shechter et al. (Industrial and engineering chemistry 1956, 48(1) pp. 94-97).*
Cyril Aymonier et al., Hybrids of Silver Nanoparticles With Amphiphilic Hyperbranched Macromolecules Exhibiting Antimicrobial Properties. *Chemistry Communication,* 3018-3019 (2002).
Aymonier, et al. "Hybrids of silver nanoparticles with amphiphilic hyperbranched macromolecules exhibiting antimicrobial properties"; Chem. Commun.; 2002, pp. 3018-3019; The Royal Society of Chemistry; XP-002543442.

* cited by examiner

*Primary Examiner* — Ernst Arnold
(74) *Attorney, Agent, or Firm* — The Nath Law Group; Tanya E. Harkins; Robert M. Joynes

(57) ABSTRACT

The invention relates to a medicotechnical product having an antimicrobial finish consisting of a complex material of metal nanoparticles and macromolecules, the macromolecules being at least partially formed from amphiphilically modified polyamino acids which contain amino acid units, which aside from the functional groups bonded in the peptide bond contain at least one further functional group and at least some of these groups are modified with substances bearing hydrophobic radicals via covalent bonds. The hydrophobic radicals are bonded by addition of substances bearing epoxy groups to the at least one further functional group and/or via at least one amino group of an amino acid unit bearing at least one amino group as a further functional group with maintenance of an amino function on the polyamino acids. The invention furthermore relates to the production of the complex material and of the medicotechnical product.

23 Claims, No Drawings

ANTIMICROBIAL MEDICOTECHNICAL PRODUCT, PROCESS FOR ITS PRODUCTION AND USE

This application is based upon and claims the benefit of priority from German Patent Application No. 10 2007 012 253.7, filed on Mar. 9, 2007, the entire contents of which are incorporated herein by reference.

The invention relates to a medicotechnical product having an antimicrobial finish, a process for its production and the use of the antimicrobial finish as a biocide in medicotechnical products.

The permanently increasing demands on hygiene standards in recent years are leading, in particular in the field of medicine, to a considerable need for antimicrobial materials. As common consumer materials, for example wood, ceramic, plastic, glass or steel themselves have no antimicrobial properties, they must be rendered antimicrobial.

A highly productive approach for this is based on "contact-active systems", where materials are provided with an antimicrobial modification such that microorganisms are destroyed on contact with the modified material without releasing, in contrast to the likewise customary release systems, an antimicrobial compound which is only present for a restricted time. Contact-active systems mainly consist of grafted antimicrobial polymers, in particular polycationic polymers having ammonium, pyridinium, biguanidine, sulfonium or phosphonium groups. However, the application of the polymers to the material concerned not uncommonly necessitates complicated surface modifications. For instance, it is known from US 2004/0171978 A1 that for the immobilization of polylysine on a polymer surface a sulfonation of the surface is first carried out. Moreover, a few contact-active systems are only restrictedly capable of employment for medical applications on account of toxic properties of some antimicrobial polymers.

In the medical and clinical field, high demands exist, however, on the biocompatibility of materials, in particular of those which are intended for surgical use. Often, there therefore remains only a small gap between antimicrobial activity and biocompatibility of the material concerned.

It is therefore the object of the present invention to make available medicotechnical products having high antimicrobial activity on the one hand and high biocompatibility on the other hand.

In WO 2004/056404, a combination of metal nanoparticles and macromolecules in the form of a polycationic biopolymer is described, which inter alia can also comprise poly-ε-lysine. Poly-ε-lysine indeed has good binding power for metals in nanoparticle form, such as, for example, silver. The combination, however, can barely be dissolved in organic solvents, in particular nonpolar organic solvents, whereby processing is made difficult. The same results from WO 2004/056403.

In an older, not previously published patent application DE 10 2005 044 360.5, it is proposed to modify polyamino acids amphiphilically in order thereby to make them dissolvable in organic nonpolar solvents and in particular the combination of polyamino acid and metal nanoparticles. Good results were achieved therewith. However, it is desired to improve these results further, in particular as far as the absorptive power to metal nanoparticles is concerned.

This object is achieved by a medicotechnical product having an antimicrobial or biocidal finish consisting of a complex material of metal nanoparticles and macromolecules, the macromolecules being at least partially formed from a polyamino acid which is amphiphilically modified in a particular manner.

The invention relates to a medicotechnical product having an antimicrobial finish consisting of a complex material of metal nanoparticles and macromolecules, the macromolecules being at least partially formed from amphiphilically modified polyamino acids which contain amino acid units, which aside from the functional groups bonded in the peptide bond contain at least one further functional group and at least some of these groups are modified with substances bearing hydrophobic radicals via covalent bonds.

The uniqueness in the invention compared to the older previously unpublished application lies in the fact that the hydrophobic radicals are bonded by reaction of substances bearing at least one epoxy group with the at least one further functional group and/or with at least one amino group of an amino acid unit bearing at least one amino group as a further functional group with maintenance of an amino function on the polyamino acids.

In the older unpublished application, the bonding of the hydrophobic radicals to the additional functional groups of the polyamino acids takes place by coupling of acid chlorides, in particular fatty acid chlorides. Esters, thioesters and in particular amides thereby result as bonding groups. The use of functional groups involved thereby involves a decrease in the absorptive power of metal nanoparticles. Therefore, an area of the modification is chosen which brings a satisfactory solubility in nonpolar organic solvents (e.g. toluene) and on the other hand guarantees an adequate absorptive power for metal particles.

According to the invention, it is on the other hand proposed to restrict the functional group in its function as little as possible. Therefore a hydrogen atom or another substitutable radical on the functional group is substituted only by a substance bearing the hydrophobic radical. The character of the functional group is thereby restricted as little as possible.

The substance bearing the hydrophobic radical can be connected in the following manner to an amino acid unit bearing at least one further trifunctional group

I)

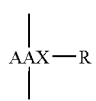

where AA is the amino acid unit of the polyamino acids. X is —O—, —S—, —COO— and in particular —N($R_1$)—, where $R_1$ is an aliphatic radical, a part of a heterocyclic ring and in particular H. R is the hydrophobic radical. This can be an aliphatic radical having 8 to 24 carbon atoms. Preferably, the radical R has the following formula

II)

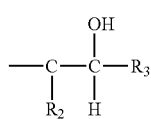

$R_2$ is a hydrophobic, in particular aliphatic, radical having 1 to 10 carbon atoms and in particular hydrogen. $R_3$ is a hydrophobic, in particular aliphatic radical having 8 to 24 carbon atoms or

III)

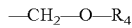

where $R_4$ is a hydrophobic, in particular aliphatic radical having 8 to 24 carbon atoms, which can be linear or branched.

The substitution according to the formula II is a substitution on the further functional group by a hydrophobic substance bearing an epoxy group, in particular one having a terminal epoxy group.

A substitution according to a combination of the formulae II and III is an epoxy substitution using a glycidyl ether. A substitution of this type for modification is preferred, because glycidyl ethers can easily be prepared on the one hand and on the other hand biodegradation via glycerol and an alcohol is possible. The epoxy compound can also be a diepoxide, in particular a diglycidyl diether.

An antimicrobial or biocidal finish within the meaning of the present invention should be understood as meaning a finish which prevents cell growth and/or proliferation of microorganisms, in particular of pathogens (harmful microorganisms), and/or brings about the destruction of existing microorganism colonies, in particular harmful microorganism colonies or biofilms.

According to one embodiment of the medico-technical product, the antimicrobial finish is provided in the form of a complex material having antimicrobial properties at least on a part of the surface of the product, in particular in the form of a coating. The antimicrobial finish is preferably present on at least one part of the surface of the product, in particular in the form of a coating. Preferably, the antimicrobial finish extends over the entire surface of the medicotechnical product. The medicotechnical product equipped in this way is advantageously distinguished in that an adequately stable adhesive connection exists between the finish and the surface of the product material, such that, for example, detachment, in particular wiping off or washing off, of the finish from the coated product is prevented and thus a medium-term, long-term and effective prevention of the medicotechnical product against microbial colonization, in particular after application has taken place, is guaranteed. The adhesive connection can be based on electrostatic attractive forces, hydrogen bonds and/or lipophilic interactions, in particular van der Waals' forces.

Additionally or alternatively to the embodiment just described, it can be provided according to the invention for the complex material to be located within the product. This can be particularly advantageous if the material of the medicotechnical product is a polymer or alternatively another material whose production process allows the introduction of the complex material into the interior of the product. In this manner, a uniformly dispersed antimicrobial activity of the medicotechnical product can be achieved.

In a further embodiment, each metal nano-particle is surrounded by at least one polyamino acid, each metal nanoparticle preferably being surrounded on all sides in a shell-like manner by at least one polyamino acid. Preferably, the polar, in particular charged, part of the polyamino acid is oriented toward the metal nanoparticles and makes possible coordinative or donative bonds to the metal nanoparticles on account of the heteroatoms or heteroatom groups, for example nitrogen and/or oxygen atoms, located in the polar part. According to the invention, the metal nanoparticles can be partially positively charged in this manner. The modified polyamino acid is a matrix for the metal particles on the medicotechnical product.

The polyamino acids can in particular be homo- or heteropolyamino acids, homopolyamino acids being particularly preferred. In the case of heteropolyamino acids, those are preferred which carry a high proportion of amino groups as a further functional group.

Also in the case of the homopolyamino acids, those having amino groups are preferred, as the amino groups favors the bonding of the metal particles. The poly-amino acids can consist of naturally occurring and/or synthetic amino acids, naturally occurring amino acids, in particular α-aminocarboxylic acids, in particular α-aminocarboxylic acids having an L configuration, being preferred. Preferably, at least a part of the amino acids are at least trifunctional amino acids. A trifunctional amino acid within the meaning of the present invention should be understood as meaning an amino acid which, additionally to the carboxyl and α-amino group, has a further organic functional group, in particular a further carboxyl, hydroxyl, thiol, guanidine or amino group, preferably a further amino group. Preferably, the polyamino acids contain at least one amino acid bearing a basic, acidic and/or sulfur-containing group. The sulfur-containing group can in particular be thiol and/or thioether groups. Particularly preferably, the polyamino acids contain at least one amino acid from the group comprising cysteine, methionine, tryptophan, histidine, arginine, lysine, ornithine, aspartic acid, glutamic acid and their derivatives. Preferably, at least 50% of the amino acid units of the polyamino acids are amino acids of this type, ornithine and in particular lysine being preferred. The remaining amino acids can be amino acids without additional functional groups, in particular alanine, valine, leucine, isoleucine and/or phenyl-alanine.

The polyamino acid can have a linear structure. The linear structure allows a tight arrangement around the metal nanoparticles to be stabilized, the arrangement in particular being stabilized by electrostatic forces, hydrogen bonds and/or lipophilic interactions, in particular van der Waals' forces.

In another preferred embodiment of the invention, the polyamino acids have a branched, preferably a hyperbranched, structure. In the preparation of the polyamino acids, internal cross-linking can also take place. The branched and/or crosslinked structure in particular allows a compact arrangement around the metal nanoparticles to be stabilized. The branched polyamino acids have at least partially globular structure, by means of which, in particular, the stabilization of the metal nanoparticles is increased. Furthermore, the branched structure of the polyamino acids advantageously brings about a decreased friability of the complex material of the product according to the invention. Thus branched and/or crosslinked polyamino acids preferably increase the film-forming properties of the complex material. Various polyamino acids can also be present as a mixture.

In a preferred embodiment of the invention, the macromolecules consist of the polyamino acids. Furthermore, the polyamino acids are particularly advantageously formed exclusively from amino acids having at least one further functional group. In turn, polyamino acids are preferred which in the still unmodified state exclusively consist of amino acid units in which the at least one further functional group is a nucleophilic group, in particular an amino group.

As further functional groups, primary amino groups are particularly preferred. These are converted into secondary amino groups in the substitution according to the invention. Secondary amino groups of this type additionally contribute to the metal bonding, since the very good binding power of primary amino groups is barely restricted by the conversion to secondary amino groups. In a corresponding manner, in a particularly preferred embodiment of the invention at least 50% of the further functional groups of the polyamino acids are primary amino groups.

According to a preferred embodiment of the medicotechnical product, the polyamino acid is polylysine, in particular poly-α-lysine (poly-alpha-lysine) and/or poly-ε-lysine (polyepsilon-lysine). Both poly-α-lysine and poly-ε-lysine have antimicrobial properties, poly-ε-lysine being more biocompatible in contrast to poly-α-lysine and therefore being particularly preferred.

The unmodified polyamino acid, in particular the polylysine, of the product according to the invention preferably has a molecular weight in the range from 500 to 1 000 000 g/mol, in particular 3000 to 100 000 g/mol. The molecular weight range desired in each case can be adjusted by the type of preparation of the polyamino acid.

In the medicotechnical product according to the invention, the polyamino acid is amphiphilically modified with a substance containing at least one hydrophobic radical, in particular with one containing at least one aliphatic radical. Such a modification serves on the one hand to increase stabilization of the metal nanoparticles and the mutual screening of the polyamino acids coordinating the nanoparticles in the solution and on the other hand to achieve good solubility in organic, in particular nonpolar solvents.

In this manner, the formation of larger nanoparticles, in particular in the form of aggregates, can be prevented. Furthermore, the formation of aggregates of polyamino acids can be avoided. Preferably, the hydrophobic radical after modification of the polyamino acid is in particular oriented outward away from the metal nanoparticles. The structure of metal nanoparticles and amphiphilically modified polyamino acids thus obtained can be designated as a "core-shell structure" (core-shell particle), where the polyamino acids immediately surrounding the metal nanoparticles are the core and the hydrophobic substance is the shell of the structure. Amphiphilicity within the meaning of the present invention should be understood as meaning the property of a compound which, on account of its molecular structure, has both hydrophilic and lipophilic properties. A complex having a core-shell structure is known, in particular, from DE 103 23 597 A1, and essentially consists of amphiphilically modified polyethyleneimine.

A great advantage of the invention lies in the fact that the degree of substitution of the polyamino acids can be kept within wide limits in the course of the modification with the hydrophobic substances and at the same time, as already mentioned, a high power of absorption to metal nanoparticles is achieved. Normally, the degree of substitution in the modification lies within the bounds of 10 to 80% based on the further functional group present in the unmodified polyamino acid.

Preferably, the aliphatic radical of the substance has 8 to 24, in particular 12 to 20, preferably 16 and/or 18, carbon atoms. The aliphatic radical can be an alkyl, alkenyl and/or an alkynyl substituent, alkyl substituents, in particular unbranched alkyl substituents, being particularly preferred. Thus, alkyl substituents, in particular long-chain and preferably unbranched alkyl substituents, allow a tighter and/or more compact addition of the alkyl chains to one another and an attractive interaction with the medical product in the region of the shell of the core-shell structure. In organic solution, the alkyl substituents repel the particles from one another and thus prevent agglomeration.

According to the invention, the substance for the amphiphilic modification is at least a biocompatible substance. For the amphiphilic modification of the polyamino acid, the substance is present in an active form, in particular as an epoxide. Furthermore, it can be preferred according to the invention for the substance to be present as a mixture of various substances.

Glycidyl ethers, in particular those having aliphatic radicals, are particularly suitable as substances for the modification. On the one hand, they can be prepared in a simple manner. On the other hand, they can also be reacted with the polyamino acid in a simple manner. Their degradation, as already mentioned, is unproblematical.

Particularly suitable substances for the modification are glycidyl hexadecyl ether and glycidyl octadecyl ether.

In particular cases, it is also possible, additional to the modification with epoxides, to carry out one with fatty acid chlorides.

According to a particularly preferred embodiment of the product according to the invention, the amphiphilic modification of the polyamino acid with the substance is based on covalent bonds, in particular on amino bonds. Preferably, secondary amines are formed from the free amino groups of the polyamino acid and epoxy groups of the substance. In the case of poly-ε-lysine, the free amino groups are the α-amino groups of the polyamino acid. The medicotechnical product is preferably distinguished in that the proportion of free amino groups of the polyamino acid after the amphiphilic modification of the polyamino acid is between 0.5 and less than 50%, in particular between 10 and 40%, in particular between 20 and 40%, preferably at about 27%, based on the original free amino groups of the polyamino acid, in particular of the polylysine.

According to a further particularly preferred embodiment of the medicotechnical product, the polyamino acids are crosslinked, in particular via a poly-functional carboxylic acid, preferably citric acid. The crosslinkage is preferably based on the formation of covalent bonds, in particular amide bonds, where the amide bonds are formed by condensation between amino groups of the polyamino acid and acid groups, in particular carboxyl groups, of the crosslinking component. The crosslinkage of the polyamino acid is particularly advantageous, as in this manner spherical structures, in particular closed core-shell structures, are present after the amphiphilic modification of the crosslinked polyamino acid, and the functional groups, in particular carboxyl groups, of the crosslinking component increase the number of possible coordination sites for the metal nanoparticles. Crosslinkage is in particular advantageous in the case of linear polyamino acids. In this manner, the complexation properties for the metal nanoparticles can be improved. Furthermore, certain properties of the biocidal complex material, in particular its film-forming properties, can be improved by crosslinkage. In the case of branched polyamino acids, spherical structures are present even without crosslinkage.

Preferably, the proportion of free amino groups of the polyamino acid after crosslinkage of the polyamino acid, in particular with citric acid, is between 25 and less than 50%, in particular between 30 and 45%, preferably between 35 and 43%, based on the original total amount of amino groups of the amino acid monomers, preferably lysine monomers, used for the preparation of the polyamino acid. Preferably, a polylysine, in particular poly-ε-lysine, crosslinked with 5 mol % of citric acid with respect to the lysine monomers employed, contains a proportion of free amino groups of about 43% and a polylysine, in particular poly-ε-lysine, crosslinked with 10 mol % of citric acid with respect to the lysine monomers employed, contains a proportion of free amino groups of about 35%, based on the original total amount of amino groups of the lysine monomers used for the preparation of the polyamino acid.

In a further preferred embodiment, the proportion of free amino groups of the polyamino acid after the amphiphilic modification of the crosslinked polyamino acid is between 15 and 35%, in particular between 25 and 35%, preferably at about 30%, based on the original total amount of amino groups of the amino acid monomers, preferably lysine monomers, used for the preparation of the polyamino acid. In a particularly preferred embodiment, a polylysine, in particular poly-ε-lysine, crosslinked with 5 mol % of citric acid with respect to the lysine monomers employed, contains a proportion of free amino groups of about 32% after amphiphilic modification, and a polylysine, in particular poly-ε-lysine, crosslinked with 10 mol % of citric acid with respect to the lysine monomers employed contains a proportion of free amino groups of about 26% after amphiphilic modification, based on the original total amount of amino groups of the lysine monomers used for the preparation of the polyamino acid. The crosslinkage can in advantageously also be carried out using multifunctional epoxides, in particular using aliphatic diepoxides, the epoxy group being arranged terminally, which is preferred overall in the case of the epoxides. The crosslinkage with epoxides in turn has the advantage that the functional groups are only slightly adversely affected in their function by the epoxide addition. Moreover, the epoxide crosslinker can also contribute to the hydrophobization of the polyamino acid, i.e. to the further modification, due to the presence of a hydrophobic radical between the two epoxy groups. It is also conceivable to carry out the modification exclusively by means of a hydrophobizing crosslinkage, e.g. with hydrophobic aliphatic diglycidyl diethers having 8 to 24 carbon atoms. Epoxides, in particular diepoxides, having an intermediate cis double bond can particularly assist solubility in organic solvents due to their configuration.

In the case of the metal nanoparticles, according to the invention they can be gold, silver, copper or zinc nanoparticles, silver nanoparticles being particularly preferred. Advantageously, the metal nanoparticles have a diameter of 0.5 to 20 nm, in particular 1 to 20 nm, preferably 1 to 14 nm.

Preferably, nanosilver particles which are stabilized by amphiphilically modified polyamino acids, in particular polylysine, preferably poly-ε-lysine, have a diameter of about 6 nm, in particular after reduction with ascorbic acid. In some cases, however, it may be preferred that the nanosilver particles have a smaller diameter, in particular of about 4 nm. This is possible, for example, by reduction using the reductant $LiBHEt_3$.

According to another preferred embodiment, nanosilver particles which are stabilized by crosslinked, in particular by citric acid-crosslinked, amphiphilically modified polyamino acids, in particular polylysine, preferably poly-ε-lysine, have a diameter of about 10 nm (5 mol % of citric acid with respect to the lysine monomers employed) or about 8 nm (10 mol % of citric acid with respect to the lysine monomers employed). This can be achieved, for example, by reduction with ascorbic acid.

In some cases it may be desirable for the metal nanoparticles, in particular silver nanoparticles, of the complex material to have a diameter in the range from 2.5 to 3.5 nm. This can be achieved, for example, by use of polylysine, preferably of poly-ε-lysine. Preferably, the polylysine is crosslinked and modified with citric acid. Thus, the metal nanoparticles can have a diameter of about 3.1 nm in the case of stabilization by polylysine which is crosslinked with 5 mol % of citric acid with respect to the lysine monomers employed. In the case of the use of polylysine which is crosslinked with 10 mol % of citric acid with respect to the lysine monomers employed, the metal nanoparticles can have a diameter of about 2.7 nm.

According to the invention, it can furthermore be provided for the medicotechnical product to be a temporary or permanent implant for the human or animal body. Here, the antimicrobially finished implants are preferably catheters, joint implants, stents, screws, pins and plates. The implants can consist of metals or metal alloys. Further materials suitable for the implants are in particular plastics. The implants can be used, for example, for the repair of fractures. The implants can furthermore be nets, preferably hernia nets. Further suitable preferred implants are in particular vascular prostheses, patches, suture materials, membranes and films, for example for adhesion prophylaxis. According to the invention, it is furthermore preferred that the implants can be incontinence belts and generally textile implants. Possible textile implants are in particular woven fabric, knitted fabric, crocheted fabric, braid, mat fabric and nonwoven fabric. The biocidal finish of these implants makes it possible to introduce these even into acutely infected or infection-endangered regions of the body, as the implants themselves have an antimicrobial action owing to the finish and in this way contribute to a reduction of a present or potential infection.

In another embodiment, the medicotechnical products are medical instruments, in particular surgical scissors, forceps and clamps, and catheters or probes and further instruments, in particular for minimally invasive intervention. In this connection, the already mentioned adhesive connection of the antimicrobial finish to the surface of the medicotechnical product is particularly advantageous, as the medical instruments just described, for example, are exposed to a particularly high mechanical stress, in particular due to rubbing and wiping. The adhesion of the antimicrobial finish to the product surface is in particular due to lipophilic interactions, preferably van der Waals' forces, of the hydrophobic radicals in particular pointing away from the metal nanoparticles, in particular long-chain aliphatic radicals of the substance, with the product surface.

The medicotechnical products according to the present invention can further be products such as, for example, drainage tubes, suture materials or wound dressings. The material of the medicotechnical product is, according to a further preferred embodiment, a metal or a metal alloy, in particular titanium, stainless steel, magnesium, tantalum or an alloy thereof, magnesium and/or tantalum being particularly preferred because of their biocompatibility and resorbability.

In a further embodiment, the material of the medicotechnical product is a nonresorbable or at least partially resorbable polymer. Thus, the nonresorbable polymer can be a polyolefin, in particular polyethylene and/or polypropylene, a polyester, in particular polyethylene terephthalate and/or polybutylene terephthalate, a polyamide, in particular polyamide-6 or polyamide-6,6, or a natural fiber, in particular silk or linen. Preferably, the at least partially resorbable polymer is a completely resorbable polymer. The resorbable polymer can in particular be a polymer based on the monomers lactide, glycolide, trimethylene carbonate, para-dioxanone, ε-caprolactone and/or hydroxybutyrate, preferably in the form of a co- and/or terpolymer. According to a further embodiment, a medicotechnical product whose material is not resorbable can be coated with an at least partially resorbable, preferably completely resorbable, polymer, in particular with one of the polymers just mentioned, in order thus to influence or to regulate the entry time of liquids, in particular of body fluids, to the antimicrobial finish.

In a further embodiment, the material of the medicotechnical product is a ceramic material. Advantageously, it can be a resorbable ceramic material, in particular hydroxyapatite or tricalcium phosphate.

According to a further embodiment, the product has pores, preferably interconnecting pores. This can be particularly advantageous, as in this manner an enlarged surface area is available for the antimicrobial finish. Thus a greater amount of the biocidal or antimicrobial complex material can be applied to and, in the case of an interconnecting pore system, also within the product to be finished.

The product is advantageously sterilizable and is present, in particular, in sterilized form. Possible sterilization methods are all methods known to the person skilled in the art, in particular irradiation, heat sterilization, steam sterilization, ethylene oxide fumigation and plasma sterilization, which preferably do not adversely affect the chemical structure and/or the antimicrobial properties of the complex material, which is in particular present in the form of a core-shell structure. The medicotechnical product according to the invention is preferably present in sterile form in the use state.

The subject of the invention moreover relates to a process for the production of a medicotechnical product, the complex material, in particular in the form of a solution, being applied to the unfinished product from outside. In the solution, the metal nanoparticles, in particular silver nanoparticles, are preferably present in stabilized form according to one of the above embodiments. Such a solution is preferably prepared starting from amphiphilically modified and in particular crosslinked polyamino acids. The core-shell polymers thus prepared are dissolved in an organic solvent and loaded with the corresponding metal ion by addition of a metal salt. The solution prepared in this manner contains metal ions stabilized by amphiphilically modified and, in particular, crosslinked and/or branched polyamino acids and is suitable, in particular, for the antimicrobial finishing of medicotechnical products, in particular for the finishing of the medicotechnical products already mentioned. Preferably, the metal ions of the solution stabilized in such a way, however, are reduced to elemental metal nanoparticles in the presence of a suitable reductant, in particular vitamin C, sodium borohydride, $LiHBEt_3$ or an aldehyde. In the case of the use of $LiHBEt_3$ (Li: lithium, H: hydrogen, B: boron and Et: ethyl) as a reductant, lithium/boron species derived therefrom can lead to crosslinkage and thus to aggregation of the amphiphilically modified and in particular crosslinked polyamino acids on account of the oxophilicity of these lithium/boron species. Therefore and in particular because of its biocompatibility, the use of vitamin C as a reductant is particularly preferred. Interestingly, in the complex material according to the invention, in particular in the complex material modified by epoxides, an autoreduction of the metal ions was also observed, such that the use of a reductant can be dispensed with. As organic solvents, various alcohols, in particular isopropanol or propanol, or aromatic solvents, for example toluene or xylene, and mixtures thereof can be used.

Furthermore, it can be preferred to apply the antimicrobial complex material to the product to be finished as a solid, for example by sputtering, or in the form of a melt or of an aerosol.

Preferably, the antimicrobial complex material is applied to the surface of the unfinished product in a dipping process. Furthermore, the antimicrobial complex material can be put into and/or onto the unfinished product by swelling. For the antimicrobial finishing of, for example, suture materials, nets or tapes, it can be preferred to apply the biocidal complex material from outside to the unfinished product in the drawing process. Furthermore, the biocidal complex material can be applied to the unfinished product by effusion, spreading, stamping and spray techniques known to the person skilled in the art, in particular pressing, rolling or doctor blades.

According to a further embodiment, an at least partially resorbable, preferably completely resorbable material, preferably a polymer, in particular in the form of a solution, is applied to the surface of the product. Thus, it can be preferred for the product according to the invention to be provided in a second coating process with a second layer of a resorbable polymer after a superficial coating with the antimicrobial complex material. Preferably, a resorbable co- and/or terpolymer, in particular based on lactide, glycolide, trimethylene carbonate, hydroxybutyrate, para-dioxanone and/or ε-caprolactone, is applied as a second layer. Suitable resorbable materials are also fatty alcohols, waxes and fatty acid salts, in particular stearate. As solvents, alcohols, aliphatic esters, ketones or aromatic solvents can be employed, ethyl acetate being particularly preferred. It is furthermore possible for the resorbable polymer to be applied to the product after surface treatment of the medico-technical product, in particular after plasma activation.

Alternatively to this, the at least partially resorbable, preferably completely resorbable, polymer and the antimicrobial complex material can be applied together to the medicotechnical product to be finished in a coating process. This is particularly advantageous, as a single coating process is more economical and thus more cost-effective.

It is furthermore possible for a ceramic and/or metal coating, in particular according to one of the two last-described embodiments, to be applied to the product to be finished, e.g. by plasma deposition.

The invention furthermore relates to a process for the production of a medicotechnical product, the complex material being added, in particular in the form of a solution, to the material of the product during its preparation additionally or alternatively to the previous embodiments or, after production of the product, introduced into this by swelling. By the addition to the material of the product, a uniform dispersion of the antimicrobial complex material within the medicotechnical product and on its surface or at least in layers close to the product surface can be achieved. With respect to further details, in particular with respect to the solution and to alternative forms of addition of the antimicrobial complex material to the material of the medicotechnical product, in particular as a solid or in the form of a melt or of an aerosol, reference is made to the above description.

In a further advantageous embodiment, the antimicrobial complex material is mixed with the product material and is subsequently shaped, in particular extruded, spun, pressed, rolled, poured or blown, to give the desired product. Particularly preferably, a mixture of polymer and antimicrobial complex material is spun to give a threaded material which, depending on the type of polymer used, can be processed, in particular interwoven, crocheted or braided to give resorbable or to give nonresorbable suture material or to give a textile product.

The present invention furthermore relates to a process for the preparation of at least one polyamino acid, in particular for the production of the product according to the invention, by polymerization of amino acids with at least one component of at least trifunctional amino acids in the liquid phase, the amino acids being polymerized without use of protective groups. The polymerization, which is a polycondensation in the narrowest sense, can be carried out at elevated temperature after previous activation of the amino acids or without activation. Various polymerization processes are described subsequently. These can lead to various yields and to various polyamino acids (linear, branched, sterically pure, racemized, low molecular weight, high molecular weight).

In one embodiment of the process according to the invention, organic solvents or organic solvent mixtures are used for the preparation of the liquid phase. Advantageously, the polymerization of the amino acids is carried out in at least one solvent, selected from the group comprising dimethyl sulfoxide (DMSO), dimethylformamide (DMF), dichloromethane, tetrahydrofuran (THF), toluene, xylene and ethyl acetate.

In a preferred embodiment of the process according to the invention, the amino acids are activated by at least one substance, preferably an organic substance. Particularly advantageously, the substance used is a nitrogen-containing compound. Preferably, the amino acids are converted by reaction with the substance to particularly reactive intermediates, in particular to active esters, and thus activated. The amino acids activated in this manner can be reacted with nucleophilic groups, in particular with amino groups, of other amino acids. The polymerization of the amino acids to the polyamino acid can thereby be carried out under particularly mild reaction conditions, in particular at room temperature. Under mild conditions of this type, the stereochemistry of the amino acids is retained.

In a particular embodiment of the process according to the invention, the amino acids are activated by at least one substance from the group comprising carbodiimides, N-hydroxysuccinimide (NHS), 1-hydroxybenzotriazole (HOBT) and derivatives derived therefrom.

Furthermore, the amino acids can be activated by reaction with pentachlorophenol and/or pentafluorophenol. As carbodiimides, in particular 1-ethyl-3-(3-dimethylaminopropyl) carbodiimide (EDC) or dicyclohexyl-carbodiimide can be used. The use of EDC can in particular be preferred because of its good water solubility. For instance, the isourea derivative resulting after successful polymerization and derived from EDC can be removed from the reaction batch by simple purification steps, in particular by an aqueous extraction. In another embodiment, it can be useful to activate the amino acids for polymerization by DCC.

In some cases, the activation potential of carbodiimides, in particular of DCC, is not adequate for a satisfactory polymerization, as, for example, the intermediates activated by carbodiimides can in particular be deactivated by subsequent reactions. These undesired subsequent reactions can in particular be rearrangement reactions, whereby the activated intermediates, in particular active esters, are converted to deactivated products, in particular amide compounds, before they can polymerize to the desired polyamino acid. In cases of this type, it can be useful according to the invention to activate the amino acids by carbodiimides, in particular DCC, and a further substance. Preferably, the further substance reacts with the activated intermediates formed from the carbodiimides and the amino acids with formation of new, preferably more reactive, intermediates, in particular with formation of active esters. The more active intermediates prepared in this manner react particularly rapidly with the amino groups of the amino acids employed for the polymerization. In this manner, a deactivation of active intermediates can be avoided particularly advantageously. In particular, the preparation of a polyamino acid, for example of a polyamino acid having a desired DP (degree of polymerization), is thus possible.

In a particularly preferred embodiment of the process according to the invention, the amino acids are activated by dicyclohexylcarbodiimide (DCC) and N-hydroxysuccinimide (NHS).

In another preferred embodiment of the process according to the invention, the amino acids are activated by dicyclohexylcarbodiimide (DCC) and 1-hydroxybenzotriazole (HOBT).

Furthermore, the amino acids can be activated by thionyl chloride ($SOCl_2$) in DMF as solvent, the activation preferably being carried out by means of a DMF-catalyzed reaction with thionyl chloride ($SOCl_2$).

Furthermore, the amino acids can be polymerized by heating in liquid phase (e.g. water). Particularly advantageously, a condensation reaction between the carboxyl and amino groups of the amino acids with elimination of water and formation of amide bonds is carried out by heating. The condensation reaction is in particular carried out at a temperature (reaction temperature) between 100 and 170° C., in particular between 110 and 160° C. The linkage of the amino acid monomer is in particular carried out during a period of 8 to 96 hours, preferably during about 96 hours. Advantageously, the reaction can be conducted at different temperatures, in particular at two different temperatures. Particularly advantageously, the polymerization can be carried out at temperatures of about 160° C. and about 120° C. Preferably, the reaction batch is first brought to a temperature of about 140° C. and kept at this temperature for about 48 hours. Subsequently, the reaction batch is preferably cooled to a temperature of about 110° C. and kept at this temperature for about a further 48 hours. Preferably, concentrations between 2 and 20 mol/l, in particular between 5 and 17 mol/l, preferably a concentration of about 15 mol/l, are used as initial concentrations for the amino acids.

Furthermore, it can be preferred according to the invention for the amino acids to be activated by silylation, in particular by reaction with hexamethyl-disilazane (HMDS). As a result of the silylation, silylated amino acids are formed, the heteroatoms of the amino acids being at least partially covalently bonded by silyl groups, in particular by trimethylsilyl groups. The amino acids activated in this manner can be polymerized to the polyamino acid.

A suitable and preferred preparation method is the fermentative preparation of polyamino acids, in particular of polylysine, with the aid of bacteria. In this manner, sterically pure polyamino acids can be prepared under mild conditions.

The polyamino acids prepared can be purified, in particular, by filtration and/or dialysis. In the case of cationic, in particular polycationic, polyamino acids, the purification is carried out particularly advantageously with the aid of the "CMC (carboxymethylcellulose) method". In the CMC method, the polyamino acids preferably form stable insoluble aggregates with the polyanionic carboxymethylcellulose soluble in the aqueous-basic environment. These aggregates can be separated from the aqueous environment by filtration and in particular washed as often as desired. All impurities can thus be eliminated.

The release of the polyamino acids from the insoluble aggregates preferably takes place by acidification in an aqueous environment, as in this manner the protonated carboxymethylcellulose (CMC) remains insoluble and the polyamino acids go into solution. Optionally, when using the CMC method, the dialysis step for the purification of the polyamino acids can be dispensed with. By suitable choice of the parameters, in particular of the pH, of the concentration, of the rate of addition and of the type of carboxymethylcellulose used, it can be achieved that individual amino acids and oligomers of the polyamino acid form no aggregates with CMC and can be advantageously removed by washing steps. With the aid of the process according to the invention described above, branched, in particular hyperbranched, polyamino acids, in particular homo-polyamino acids, preferably poly-ε-lysine, are preferably prepared. With respect to further details, reference is made to the description up to now.

A summary of the various possibilities of preparation of polyamino acids as exemplified by homo- and heteropolylysine is presented in the following table.

Summary of the polymerizations of lysine

| | 1.) Classical polycondensation | 2.) Polymerization by means of EDC | 3.) Polymerization by means of DCC/NHS | 4.) Polymerization by means of CDI |
|---|---|---|---|---|
| Monomer employed | Lysine or lysine × HCl/NaOH | Lysine × HCl | Lysine/alanine | Lysine |
| Reaction medium | Water | Water | Ethyl acetate | Ethyl acetate |
| Reaction temperature (time) | 160° C. (2 d)/120° C. (2) | RT (7 d) | RT (10 d) | RT (4 d) |
| Activation reagent [eq.] | — | 1-Ethyl-3-(3-dimethylaminopropyl)carbodiimide [3.0] | Dicyclohexylcarbodiimide [1.4], N-hydroxysuccinimide [3.7] | Carbonyldiimidazole [2.6] |
| Workup | Dialysis | Dialysis | Filtration, soxhlet extraction, dialysis | Filtration, dialysis |
| Monomer units (MU) of the synthesized polymers | Lysine 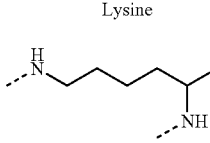 | Lysine 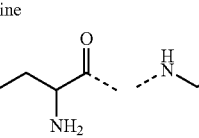 β-Alanine 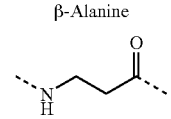 | Lysine 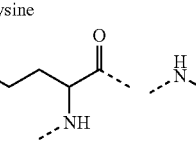 | Lysine 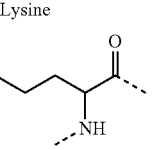 |

In a further preferred embodiment of the process according to the invention, the polyamino acid is amphiphilically modified in liquid phase. For the preparation of the liquid phase, organic solvents or solvent mixtures, in particular tertiary butanol, are in particular possible. Preferably, the polyamino acid is suspended in liquid phase, e.g. tertiary butanol, and warmed. In a preferred embodiment of the process according to the invention, the epoxide intended for the amphiphilic modification is added to the solution or suspension of the polyamino acid to be modified. The modification reaction is preferably carried out at temperatures in the range from 30 to 80° C., in particular 40 to 60° C., and the product obtained is purified by dialysis.

The invention furthermore comprises the use of a complex material of metal nanoparticles and macromolecules, the macromolecules being at least partially formed from a polyamino acid and surrounding each metal nanoparticle in particular in a shell-like manner, as a biocide in a medicotechnical product. With respect to further features and details, reference is made to the description up to now.

The product according to the invention has biocompatible, in particular tissue-compatible, and at the same time extremely efficacious antimicrobial and/or biocidal properties due to the molecular structure and the construction of its finish. The composition of the complex material of endogenous substances or of substances which are constructed from endogenous compounds and/or of at least essentially body-compatible substances guarantees the biocompatibility of the antimicrobially finished product just mentioned.

The antimicrobial properties of the finish are based both on the biocidal action of the metal nanoparticles, in particular silver nanoparticles, and on the biocidal action of the polyamino acid, in particular poly-ε-lysine. The bringing together of these antimicrobially acting substances in the form of a complex material causes its high efficacy against, in particular, harmful microorganisms or pathogens. Particularly advantageously, on the one hand the stabilization of the metal nanoparticles in nonpolar solvents can be brought about by a core-shell structure of the complex material and thus precipitation and uncontrollable accumulation of the metal can be prevented. On the other hand, the hydrophobic shell of the core-shell structure mediates the adhesion of the finish, in particular to the product surface. In this manner, the risk of an uncontrollable or alternatively a continuous release of the metal into the environment, in particular into the surrounding body tissue, can be reduced. Thus, side effects possibly occurring in this connection can be reduced or essentially prevented.

Further features of the invention result on account of the following description of preferred embodiments by means of examples. Here, the individual features of the invention can be realized alone or in combination with one another. The embodiments described serve only for explanation and for the better understanding of the invention and are in no way to be understood as restrictive.

EXAMPLE 1

Preparation of ε-Poly-L-Lysine 0.627 g of 1-ethyl-3-[3-(dimethylamino)propyl]-carbodiimide hydrochloride was added at room temperature to a solution of 0.200 g of L-lysine hydrochloride in 4 ml of water (dist.) in five portions, the reaction solution being stirred between two additions for 24 hours. After the end of polymerization, the reaction mixture was dialyzed against water (dialysis membrane with a cutoff of 2000 g/mol) and the polypeptide was subsequently obtained. (Yield: 0.016 g [9%]).

EXAMPLE 2

Polymerization of L-Lysine by Addition of DCC/NHS 566 mg (2.74 mmol, 2.0 equivalents) of dicyclohexylcarbodiimide and 316 mg (2.74 mmol, 2.0 equivalents) of N-hydroxysuccinimide (NHS) were added to a stirred colorless suspension of 200 mg of L-lysine (1.37 mmol, 1.0 equivalent) in 5 ml of ethyl acetate. The milky suspension was stirred at room temperature for 4 days and subsequently concentrated to dryness by removal of the solvent. The resulting solid was treated with 20 ml of water and the resulting colorless suspension was centrifuged (10 minutes at 4000 revolutions per minute). The colorless solid separated off was washed twice with 10 ml each of water. The combined aqueous clear phases were concentrated to about 10 ml, turbidity occurring. The resulting suspension was filtered and the filtrate was dialyzed against water (MWCO 2000). From the dialysis, 55 mg of colorless poly-L-lysine (0.43 mmol of lysine units, yield: 33%) were obtained.

EXAMPLE 3

Alternative to Example 2

24.426 g of dicyclohexylcarbodiimide (0.118 mol, 1.7 eq.) and 26.963 g of N-hydroxysuccinimide (0.234 mol, 3.4 eq.) were added to a stirred colorless suspension of 10.221 g of L-lysine (0.070 mol, 1.0 eq.) in 180 ml of ethyl acetate. The milky suspension was stirred at room temperature for 10 days and subsequently concentrated to dryness by stripping off the solvent in vacuo. The resulting solid was treated with 200 ml of water and the suspension was filtered and washed with 100 and 200 ml each of water. The combined aqueous phases were concentrated, turbidity occurring, and subsequently freeze-dried. The anhydrous solid was subsequently purified by soxhlet extraction in ethanol for five days. The residue in the soxhlet sleeve was dried and dissolved in water. The residues removed from the sleeve were eliminated by filtration. The aqueous solution was dialyzed against water (MWCO 2000 g/mol), the solvent altogether being renewed seven times after every 12 h. 1.730 g of colorless polymer were obtained from the dialysis after concentration.

EXAMPLE 4

Silylation of L-Lysine with Hexamethyldisilazane (HMDS)

9.14 g of L-lysine hydrochloride (0.05 mol, 1.0 equivalent) were suspended in 53 ml of hexamethyldisilazane (41.02 g, 0.254 mmol, 5.1 equivalents) and the suspension was heated to 130° C. After 8 hours, a yellow solution was obtained. After 24 hours, the solution became dark brown. Residual hexamethyldisilazane was removed in vacuo (63° C., 20 mbar) and a dark brown oily mass was obtained. By means of distillation (90° C., 0.1 mbar), 5.68 g of colorless oil of silylated L-lysine were obtained. At a degree of silylation of 1.9 per lysine molecule, a yield of 40% with respect to the L-lysine employed was calculated.

EXAMPLE 5

Polymerization of the Silylated L-Lysine 2.860 mg of the silylated L-lysine (about 0.012 mol of lysine component and about 0.023 mol, 1.0 equivalent, of trimethylsilyl component) were heated under reflux to 80° C. and 1.0 ml of isopropanol (0.785 g, 0.013 mol, 0.6 equivalent) was slowly added dropwise thereto. An orange solid in a pale yellow liquid was slowly formed. After 8 hours, the mixture was cooled to room temperature, and a further ~1.4 ml of isopropanol were added. After one hour, 2 ml of water were added and the entire solvent and the resulting hydroxytrimethylsilane were removed in vacuo. The residue was dissolved in water and dialyzed against water (MWCO 2000). 60 mg of yellowish polymer (about 4% yield) were obtained from the dialysis.

EXAMPLE 6

Polycondensation 7.422 g of L-lysine×$H_2O$ (0.045 mol) were dissolved in 5.0 ml of water in an ultrasonic bath. Subsequently, sufficient water was removed on a rotary evaporator until turbidity occurred, which in air changed to a clear viscous solution. By differential weighing, it turned out that 3.0 ml of water remained as solvent. The aqueous L-lysine solution was heated under reflux to 160° C. (oil bath temperature) and stirred for 2 days. Subsequently, it was temperature-controlled down to 120° C. and stirred for a further 2 days. During the reaction, a gentle stream of nitrogen was regularly passed through the apparatus for a few minutes in order to remove water. After the reaction was complete, the mixture was cooled to room temperature and the very viscous orange mass was dissolved in water and subsequently dialyzed against water (MWCO 2000). 2.278 g of polymer were obtained from the dialysis (yield: about 37%).

EXAMPLE 7

Crosslinking of ε-Poly-L-Lysine by Citric Acid

Polymerization of 0.200 g of L-lysine hydrochloride (1.00 equivalent) was first carried out according to Example 1. Subsequently, after 24 hours of the last EDC addition, a freshly prepared solution of 0.011 g of citric acid (0.055 mmol, 0.05 equivalent) and 0.032 g of EDC.HCl (0.167 mmol, 0.15 equivalent) in 1 ml of water was added. For greater crosslinkage, 0.021 g of citric acid (0.110 mmol, 0.10 equivalent) and 0.064 g of EDC.HCl (0.334 mmol, 0.30 equivalent) were employed in the same procedure and an identical batch.

EXAMPLE 8

Modification of ε-Poly-L-Lysine 501.5 mg (3.912 mmol of ME, 1.00 eq.) of poly-ε-lysine (PL) were suspended in 30 ml of tert-butanol and the suspension was stirred at 50° C. under reflux. After 15 minutes, 1516.0 mg (5.079 mmol, 1.31 eq.) of glycidyl hexadecyl ether (GHE) were added. The suspension was stirred at 50° C. for a further 20 hours. After stripping off the solvent on a rotary evaporator, the dry crude product was dissolved in 50 ml of isopropanol at 40° C. and subsequently dialyzed against isopropanol (MWCO 2000 g/mol). After stripping off the solvent, 1067.3 mg of the hydrophobically modified GHE-PL were obtained from the dialysis. In the PL hydrophobically modified by GHE, a degree of modification of 73% of the free amino groups of the PL was determined by the TNBS test in which it is quantitatively tested for amino groups. Using 0.43 and 0.83 equivalents of GHE respectively, degrees of modification of 10 and 47% respectively are obtained.

EXAMPLE 9

Crosslinkage and Modification of Fermentatively Prepared Polylysine

A freshly prepared solution of 38.4 mg of citric acid (0.201 mmol, 0.05 eq.) and 116.1 mg of EDC.HCL (0.604 mmol, 0.15 eq.) in 3 ml of deionized water was added to a solution of 500.3 mg of ε-lysine (3.903 mmol of ME, —$NH_2$, 1.00 eq., Chisso Corp. Japan, Lot. D3050804) in 10 ml of deionized water. The mixture was subsequently stirred at room temperature for 24 h and then concentrated and lyophilized.

The crude product (about 3.32 mmol of —$NH_2$, 1.00 eq.) was suspended in 30 ml of tertiary butanol and the suspension was refluxed at 50° C. After 15 minutes, 1301.1 mg (4.359 mmol, about 1.31 eq.) of glycidyl hexadecyl ether were added and the suspension was stirred at 50° C. for a further 20 h. After stripping off the solvent, the dry crude product was dissolved in 50 ml of isopropanol at 40° C. and the solution was subsequently dialyzed against isopropanol (MWCO 2000 g/mol). After stripping off the solvent, the desired polymer (citric acid-crosslinked and GEHE-modified ε-polylysine) were obtained from the dialysis.

EXAMPLE 10

Loading of the Polymer Articles with Silver(I) Nitrate and Reduction 10 mg of modified ε-poly-L-lysine were dissolved in 7.6 ml of toluene under a nitrogen atmosphere and 5.7 mg of $AgNO_3$ were added in three portions (stirring time of 24 hours after each addition). A clear and stable silver(I) polymer-toluene solution was obtained. 0.1 ml of the silver(I) polymer-toluene solution (contents: 0.13 mg of polymer, 0.05 mg of $AgNO_3$) was diluted with 2 ml of i-propanol and treated with 0.03 ml of a 0.02 M L-ascorbic acid solution (in i-propanol). The solution turned intensively yellow. Alternatively, 0.1 ml of the silver(I) polymer-toluene solution (contents: 0.13 mg of polymer, 0.05 mg of $AgNO_3$) can be diluted with 2 ml of i-propanol and treated with 0.06 ml of a dilute 0.01 M (M: molarity) Li[$HBEt_3$] solution (in THF). The solution likewise turns intensively yellow.

EXAMPLE 11

Loading of the Polymer Articles with Silver(I) Nitrate without Reductant

The GHE-PL from Example 8 was dissolved in toluene under an argon atmosphere and silver nitrate ($AgNO_3$) was added in portions. In this way, it was possible to dissolve 19.03 mg of silver nitrate in 50.0 mg of GHE-PL (corresponds to 38.1% by weight). The absorbability of silver was increased sixfold in this case in comparison to a modification containing fatty acids. A further advantage of the GHE modification consists in the self-reducing properties. On loading GHE-PL with silver nitrate, after some time the yellow to brown coloration of the silver nanoparticles occurs. Silver nitrate can thus be reduced in GHE-PL without addition of reductants. The reduction of the ionic silver to neutral silver takes place with simultaneous oxidation of the hydroxyl group, formed from the epoxy group and adjacent to the secondary amino group, to the keto group. This self-reduction can be further assisted by supply of heat (1 h at 90° C.). The reduction of the silver nitrate can also be accelerated, if desired, by addition of reductants such as, for example, of ascorbic acid.

EXAMPLE 12

Preparation of Films on Glass Slides

For the preparation of a film, a silver(0) polymer solution was applied with a pipette to a labeled area of about 1 $cm^2$ of a glass slide serving as a model for a medical product. The slide was placed on a heated plate and the solvent was evaporated. In the course of this, the solution on the glass, which was becoming more and more concentrated, was stirred with the pipette such that a film was formed in the labeled zone. The complex of metal nanoparticles and modified polyamino acid can be sterilized, e.g. heat-sterilized (4 h at 180° C.), as such or together with the medical product.

EXAMPLE 13

Bacterial Tests

For the bacterial tests, films about 1 $cm^2$ in size were prepared on glass slides: 4 μg of silver in 40 μg of polymer or 10 μg of silver in 100 μg of polymer. For the preparation of the bacterial cells, 50 ml of a sterile standard culture medium from Merck were inoculated with 100 μl of suspension of *Staphylococcus aureus* cells (about $10^{11}$ cells per ml) in PBS (phosphate-buffered saline, pH 7.0) and incubated with shaking at 37° C. for 6-hours. After centrifuging the bacterial suspension, the cells were washed twice with PBS (pH 7.0), then resuspended using PBS and diluted further with PBS to a concentration of $5\times10^8$ cells per ml. The cell concentration was checked by the absorption at 600 nm. The prepared films were washed in PBS for 2 minutes and sprayed with the bacterial suspension. Subsequently, the slides were placed in one petri dish each and 25 ml of growth agar (1.5% by weight of agar in growth medium was heated at 100° C. for minutes and rapidly cooled to 40° C.) were added. The petri dishes were then incubated at 37° C. The films containing a minimum amount of silver of 10 μg per $cm^2$ prevented the growth of the *Staphylococcus aureus* cells sprayed on to an extent of more than 99%.

The invention claimed is:

1. A medicotechnical product having an antimicrobial finish consisting of a complex material of metal nanoparticles and macromolecules, the macromolecules are formed from amphiphilically modified polyamino acids which contain amino acid units, which aside from the functional groups bonded in the peptide bond contain at least one further functional group and at least some of these groups are modified with first substances bearing hydrophobic radicals via covalent bonds, the hydrophobic radicals being bonded by reaction of second substances bearing at least one epoxy group with the at least one further functional group and/or with at least one amino group of an amino acid unit bearing at least one amino group as a further functional group with maintenance of an amino function on the polyamino acids.

2. The medicotechnical product as claimed in claim 1, the finish being provided at least on one part of the surface of the product.

3. The medicotechnical product as claimed in claim 1, the finish being provided in the interior of the product.

4. The medicotechnical product as claimed in claim 1, each metal nanoparticle being surrounded by at least one modified polyamino acid.

5. The medicotechnical product as claimed in claim 1, the polyamino acids being homo- and/or hetero polyamino acids.

6. The medicotechnical product as claimed in claim 1, the polyamino acids consisting of naturally occurring and/or synthetic amino acid units.

7. The medicotechnical product as claimed in claim 1, the polyamino acids containing at least one basic, acidic and/or sulfur-containing amino acid unit selected from the group consisting of cysteine, methionine, tryptophan, histidine, arginine, lysine, ornithine, aspartic acid, glutamic acid and their derivatives, and wherein at least 50% of the amino acid units of a polyamino acid being formed from amino acid units of this type.

8. The medicotechnical product as claimed in claim 1, the polyamino acids having a linear structure.

9. The medicotechnical product as claimed in claim 1, the polyamino acids being branched, polyamino acids.

10. The medicotechnical product as claimed in claim 1, the polyamino acids being exclusively formed from amino acids having at least one further functional group.

11. The medicotechnical product as claimed in claim 1, the unmodified polyamino acids consisting exclusively of amino acid units in which the at least one further functional group is a nucleophilic group, having an amino group, and wherein the amino group being a primary amino group which is converted into a secondary amino group radical by addition of the hydrophobic radical.

12. The medicotechnical product as claimed in claim 1, the polyamino acid being polylysine.

13. The medicotechnical product as claimed in claim 1, the still unmodified polyamino acid having a molecular weight in the range from 500 to 1 000 000 g/mol.

14. The medicotechnical product as claimed in claim 1, the polyamino acid being amphiphilically modified by at least one glycidyl ether having at least one aliphatic radical.

15. The medicotechnical product as claimed in claim 1, the hydrophobic radical being a linear aliphatic radical having an even number of carbon atoms.

16. The medicotechnical product as claimed in claim 1, the hydrophobic radical having 8 to 24 carbon atoms.

17. The medicotechnical product as claimed in claim 14, the glycidyl ether being glycidyl hexadecyl ether and/or glycidyl octadecyl ether.

18. The medicotechnical product as claimed in claim 1, the unmodified polyamino acid having a globular structure.

19. The medicotechnical product as claimed in claim 1, the polyamino acids being crosslinked with a crosslinking component.

20. The medicotechnical product as claimed in claim 1, the metal nanoparticles selected from the group consisting of gold, silver, copper and zinc nanoparticles.

21. The medicotechnical product as claimed in claim 1, the metal nanoparticles having a diameter of 0.5 to 20 nm.

22. A process for the production of the medicotechnical product as claimed in claim 1, the antimicrobial finish being applied, in the form of a solution, to the unfinished product from outside and/or being introduced into the material of the product during its production.

23. A complex material consisting of metal nanoparticles and macromolecules, the macromolecules are formed from amphiphilically modified polyamino acids, which aside from the groups bonded in the peptide bond contain at least one further functional group and at least some of these further functional groups are modified by means of covalent bonds with first substances bearing hydrophobic radicals, the hydrophobic radicals being bonded by addition of second substances bearing epoxy groups to the at least one further functional group and/or by means of at least one amino group of an amino acid unit bearing at least one amino group as a further functional group with maintenance of an amino function on the polyamino acids.

* * * * *

UNITED STATES PATENT AND TRADEMARK OFFICE
CERTIFICATE OF CORRECTION

PATENT NO. : 8,105,619 B2
APPLICATION NO. : 12/073560
DATED : January 31, 2012
INVENTOR(S) : Odermatt et al.

Page 1 of 1

It is certified that error appears in the above-identified patent and that said Letters Patent is hereby corrected as shown below:

Add 2nd assignee as follows:

(73) Assignee: AESCULAP AG & CO. KG, Tuttlingen/Donau
(DE)

ALBERT-LUDWIGS-UNIVERSITÄT FREIBURG, Freiburg
(DE)

Signed and Sealed this
Twenty-sixth Day of June, 2012

David J. Kappos
*Director of the United States Patent and Trademark Office*

UNITED STATES PATENT AND TRADEMARK OFFICE
CERTIFICATE OF CORRECTION

PATENT NO. : 8,105,619 B2
APPLICATION NO. : 12/073560
DATED : January 31, 2012
INVENTOR(S) : Odermatt et al.

It is certified that error appears in the above-identified patent and that said Letters Patent is hereby corrected as shown below:

On the Title Page

Add 2nd assignee as follows:

(73) Assignee: AESCULAP AG, Tuttlingen/Donau
(DE)

ALBERT-LUDWIGS-UNIVERSITÄT FREIBURG, Freiburg
(DE)

This certificate supersedes the Certificate of Correction issued June 26, 2012.

Signed and Sealed this
Thirteenth Day of May, 2014

Michelle K. Lee
*Deputy Director of the United States Patent and Trademark Office*